US010941089B2

United States Patent
Jungong et al.

(10) Patent No.: US 10,941,089 B2
(45) Date of Patent: Mar. 9, 2021

(54) PROCESSES FOR PRODUCING TRIFLUOROIODOMETHANE USING TRIFLUOROACETIC ACID

(71) Applicant: Honeywell International Inc., Morris Plains, NJ (US)

(72) Inventors: Christian Jungong, Depew, NY (US); Haiyou Wang, Amherst, NY (US); Terris Yang, East Amherst, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 16/797,696

(22) Filed: Feb. 21, 2020

(65) Prior Publication Data
US 2020/0283358 A1 Sep. 10, 2020

Related U.S. Application Data

(60) Provisional application No. 62/813,507, filed on Mar. 4, 2019.

(51) Int. Cl.
C07C 17/361 (2006.01)
(52) U.S. Cl.
CPC ........ *C07C 17/361* (2013.01); *C07C 2523/06* (2013.01); *C07C 2523/72* (2013.01); *C07C 2523/745* (2013.01)
(58) Field of Classification Search
CPC .............. C07C 17/361; C07C 2523/06; C07C 2523/745; C07C 2523/72; C07C 19/16
See application file for complete search history.

(56) References Cited

U.S. PATENT DOCUMENTS

2006/0122440 A1 6/2006 Mukhopadhyay et al.
2008/0108854 A1* 5/2008 Yang ........................ B01J 23/78
570/174

FOREIGN PATENT DOCUMENTS

CN 108246277 A 7/2018

OTHER PUBLICATIONS

Hongying et al, Trifluoroiodomethane preparation, CN 102992943, machine translation Jun. 2015.*
Clark et al., Trifluoromethyl Complexes of Osmium(11) by Halogen Oxidation of an Osmium(0) Difluorocarbene Compound and the Structures of Os(CF3)Cl2(NO)(PPh3)2 and Os(CF3)C10.66611.333(NO)(PPh3)2, Australian Journal of Chemistry, vol. 39, 1986, pp. 1315-1320.
Fu et al., "Cu-catalyzed decarboxylative iodination of aryl carboxylic acids with NaI: A practical entry to aryl iodides under aerobic conditions", Tetrahedron Letters, 2018, vol. 59, pp. 4458-4461.
International Search Report and Written Opinion received for PCT Patent Application No. PCT/US2020/020724, dated Jun. 29, 2020, 12 pages.
Lee et al., "Synthesis of CF3I by Direct Iodination of CF3COOH on Solid Catalyst", Journal of the Korean Institute of Chemical Engineers, Apr. 2001, vol. 39, No. 2, pp. 144-149.

* cited by examiner

*Primary Examiner* — Jafar F Parsa
(74) *Attorney, Agent, or Firm* — Faegre Drinker Biddle & Reath LLP

(57) ABSTRACT

The present disclosure provides a process for producing trifluoroiodomethane by reacting trifluoroacetic acid, an iodine source, and a metal fluoride in the presence of a metal catalyst to produce trifluoroiodomethane.

18 Claims, No Drawings

PROCESSES FOR PRODUCING TRIFLUOROIODOMETHANE USING TRIFLUOROACETIC ACID

CROSS-REFERENCE TO RELATED APPLICATIONS

This application is a U.S. Nonprovisional Application which claims priority to Provisional Application No. 62/813,507, filed Mar. 4, 2019, which is incorporated herein by reference in its entirety.

FIELD

The present disclosure relates to processes for producing trifluoroiodomethane ($CF_3I$). Specifically, the present disclosure relates to methods to produce trifluoroiodomethane from trifluoroacetic acid.

BACKGROUND

Trifluoroiodomethane ($CF_3I$) is a useful compound in commercial applications, as a refrigerant or a fire suppression agent, for example. Trifluoroiodomethane is an environmentally acceptable compound with a low global warming potential and low ozone depletion potential. Trifluoroiodomethane can replace more environmentally damaging materials.

Methods of preparing trifluoroiodomethane from trifluoroacetic acid are known. However, the methods require a two-step process in which the trifluoroacetic acid is converted to a metal trifluoroacetate in a first step, and the metal trifluoroacetate and iodine are converted to trifluoroiodomethane in a second step. For example, Chinese Patent CN102992943B discloses reacting trifluoroacetic acid with a metal oxide in a first step to produce metal trifluoroacetate, and then reacting metal trifluoroacetate and elemental iodine in a second step to produce trifluoroiodomethane, carbon dioxide, and metal iodide.

Thus, there is a need to develop one-step methods that are more efficient and economical in the production of trifluoroiodomethane from trifluoroacetic acid.

SUMMARY

The present disclosure provides one-step processes for producing trifluoroiodomethane by reacting trifluoroacetic acid, an iodine source, and a metal fluoride in the presence of a metal catalyst to produce trifluoroiodomethane.

In one embodiment, the present invention provides a process for producing trifluoroiodomethane ($CF_3I$). The process includes providing trifluoroacetic acid, an iodine source, a metal catalyst, a metal fluoride and a solvent, and reacting the trifluoroacetic acid, the iodine source, and the metal fluoride in the presence of the metal catalyst and the solvent to produce trifluoroiodomethane.

In another embodiment, the present invention provides a process for producing trifluoroiodomethane ($CF_3I$). The process includes mixing trifluoroacetic acid, an iodine source, a metal catalyst, a metal fluoride, and a solvent, and heating the trifluoroacetic acid, the iodine source, the metal catalyst, the metal fluoride, and the solvent to react the trifluoroacetic acid, the iodine source, and the metal fluoride to produce trifluoroiodomethane and a metal salt.

The above mentioned and other features of the disclosure, and the manner of attaining them, will become more apparent and will be better understood by reference to the following description of embodiments.

DETAILED DESCRIPTION

The present disclosure provides a liquid phase process for the manufacture of trifluoroiodomethane ($CF_3I$) from trifluoroacetic acid ($CF_3COOH$) and an iodine source, such as iodine ($I_2$) or iodine monochloride (ICl), by decarboxylative iodination in the presence of a metal fluoride and a catalyst in a single-step method according to Equation 1 below:

$$CF_3COOH + IX + MF \xrightarrow{\text{CATALYST}} CF_3I + CO_2 + HF + MX \quad \text{Eq. 1}$$

where M is an alkali metal, such as lithium, potassium, or sodium, or an alkaline earth metal, such as calcium or magnesium; X is a halogen, such as fluorine, chlorine, bromine, or iodine. The process eliminates the need to convert trifluoroacetic acid to a metal trifluoroacetate in a separate step.

Without wishing to be bound by any theory, it is believed that under the reaction conditions described below, the single step of Equation 1 is realized as the trifluoroacetic acid ($CF_3COOH$) decomposes to form hydrofluoric acid (HF) and a difluorocarbonyl radical, which further decomposes to form a difluorocarbene. The difluorocarbene reacts with the metal fluoride (MF) to form a trifluoromethyl anion complex which then reacts with the iodine source (IX) to form trifluoroiodomethane ($CF_3I$). In the absence of the metal fluoride (MF), it is believed that the difluorocarbene undergoes competing reactions by means of disproportionation, with little, if any, of the difluorocarbene forming trifluoroiodomethane.

The reaction is carried out with a catalyst, such as a metal catalyst. Metal catalysts useful for carrying out the reaction in the liquid phase have been found to include copper (I) iodide (CuI), ferrous chloride ($FeCl_2$) and zinc (II) iodide ($ZnI_2$). Copper (I) iodide, ferrous chloride and zinc (II) iodide are commercially available and can be obtained from Sigma-Aldrich Corp., St. Louis, Mo.

The catalyst may be provided for the reaction at a mole percent of the trifluoroacetic acid as low as about 0.5%, about 1%, about 2%, about 5%, about 10%, about 15%, about 20% or about 25%, or as high as about 30%, about 35%, about 40%, about 45%, or about 50%, or within any range defined between any two of the foregoing values, such as about 0.5% to about 50%, about 2% to about 45%, about 5% to about 40%, about 10% to about 35%, about 15% to about 30%, or about 20% to about 30%, for example. Preferably, the catalyst is provided at a mole percent of the trifluoroacetic acid from about 0.5% to about 35%. More preferably, the catalyst is provided at a mole percent of the trifluoroacetic acid from about 10% to about 30%. Most preferably, the catalyst is provided at a mole percent of the trifluoroacetic acid from about 20% to about 30%.

The reaction is carried out in a solvent. Solvents useful for carrying out the reaction in the liquid phase include dimethylformamide, dimethyl sulfoxide, ionic liquids, polar aprotic solvents, or combinations thereof. Examples of ionic liquids include imidazolium salts and caprolactamium hydrogen sulfate. Examples of polar aprotic solvents with high boiling points include sulfolane, N,N-dimethylacetamide, N-methyl-2-pyrrolidone (NMP), and dimethyl sulfone.

The solvent is substantially free of water. Substantially free of water means that the amount of water in the solvent is less than about 500 parts per million (ppm), about 300 ppm, about 200 ppm, about 100 ppm, about 50 ppm, about 30 ppm, about 20 ppm, or about 10 ppm, or less than any value defined between any two of the foregoing values. The foregoing ppm values are by weight of the solvent and any water. Preferably, the amount of water in the solvent is less than about 100 ppm. More preferably, the amount of water in the solvent is less than about 50 ppm. Most preferably, the amount of water in the solvent is less than about 10 ppm.

Trifluoroacetic acid and iodine are readily available in commercial quantities. For example, trifluoroacetic acid and iodine may be obtained from Sigma-Aldrich Corp., St. Louis, Mo. The solvents may also be readily obtained in commercial quantities. For example, sulfolane may also be obtained from Sigma-Aldrich Corp., St. Louis, Mo. The metal fluorides are also readily available in commercial quantities. It is preferred that the metal fluoride be in a spray-dried powder form. The spray-dried powder has a large surface area, reduced moisture sensitivity, and enhanced reactivity. It has been found that metal fluorides that are not in a spray-dried powder form resulted in little or no reaction. For example, potassium fluoride may be obtained in a spray-dried powder form from Honeywell Research Chemicals.

The iodine source may include elemental iodine ($I_2$), iodine monochloride (ICl), iodine monofluoride (IF), iodine monobromide (IBr), or combinations thereof. The iodine source may consist of elemental iodine ($I_2$), iodine monochloride (ICl), iodine monofluoride (IF), iodine monobromide (IBr), or combinations thereof. The iodine source may include elemental iodine ($I_2$). The iodine source may include iodine monochloride (ICl). The iodine source may include iodine monofluoride (IF). The iodine source may include iodine monobromide (IBr). The iodine source may consist of elemental iodine ($I_2$). The iodine source may consist of iodine monochloride (ICl). The iodine source may consist of iodine monofluoride (IF). The iodine source may consist of iodine monobromide (IBr).

The trifluoroacetic acid and iodine source may be provided for the reaction at a mole ratio of trifluoroacetic acid to iodine source as low as about 0.1:1, about 0.2:1, about 0.3:1, about 0.4:1, about 0.5:1, about 0.6:1, about 0.7:1, about 0.8:1, about 0.9:1, about 0.95:1, about 0.99:1, or about 1:1, or as high as about 1.01:1, about 1.05:1, about 1.1:1, about 1.2:1, about 1.3:1, about 1.4:1, about 1.5:1, about 1.6:1, about 1.8:1, or about 2.0:1, or within any range defined between any two of the foregoing values, such as about 0.1:1 to about 2.0:1, about 0.5:1 to about 1.5:1, about 0.6:1 to about 1.4:1, about 0.7:1 to about 1.3:1, about 0.8:1 to about 1.2:1, about 0.9:1 to about 1.1:1, about 0.95:1 to about 1.05:1, about 0.99:1 to about 1.01:1, about 1:1 to about 2:1, about 0.8:1 to about 1.5:1, or about 0.95:1 to about 1.2:1, for example. Preferably, the mole ratio of trifluoroacetic acid to the iodine source is from about 0.8:1 to about 1.5:1. More preferably, the mole ratio of trifluoroacetic acid to the iodine source is from about 1:1 to about 1.2:1. Most preferably, the mole ratio of trifluoroacetic acid to the iodine source is about 1:1.

The metal fluoride may include potassium fluoride, sodium fluoride, lithium fluoride, rubidium fluoride, calcium fluoride, magnesium fluoride, or combinations thereof. The metal fluoride may consist essentially of potassium fluoride, sodium fluoride, lithium fluoride, rubidium fluoride, calcium fluoride, magnesium fluoride, or combinations thereof. The metal fluoride may consist of potassium fluoride, sodium fluoride, lithium fluoride, rubidium fluoride, calcium fluoride, magnesium fluoride, or combinations thereof. The metal fluoride may consist of potassium fluoride. The metal fluoride may consist of sodium fluoride. The metal fluoride may consist of lithium fluoride. The metal fluoride may consist of rubidium fluoride. The metal fluoride may consist of calcium fluoride. The metal fluoride may consist of magnesium fluoride.

The metal fluoride may be provided for the reaction at a mole ratio of trifluoroacetic acid to metal fluoride as low as about 0.1:1, about 0.2:1, about 0.3:1, about 0.4:1, about 0.5:1, about 0.6:1, about 0.7:1, about 0.8:1, about 0.9:1, about 0.95:1, about 0.99:1, or about 1:1, or as high as about 1.01:1, about 1.05:1, about 1.1:1, about 1.2:1, about 1.3:1, about 1.4:1, about 1.5:1, about 1.6:1, about 1.8:1, or about 2.0:1, or within any range defined between any two of the foregoing values, such as about 0.1:1 to about 2.0:1, about 0.5:1 to about 1.5:1, about 0.6:1 to about 1.4:1, about 0.7:1 to about 1.3:1, about 0.8:1 to about 1.2:1, about 0.9:1 to about 1.1:1, about 0.95:1 to about 1.05:1, about 0.99:1 to about 1.01:1, about 1:1 to about 2:1, about 0.8:1 to about 1.5:1, or about 0.95:1 to about 1.2:1, for example. Preferably, the mole ratio of trifluoroacetic acid to the metal fluoride is from about 0.8:1 to about 1.5:1. More preferably, the mole ratio of trifluoroacetic acid to the metal fluoride is from about 1:1 to about 1.2:1. Most preferably, the mole ratio of trifluoroacetic acid to the metal fluoride is about 1:1.

The reaction may be conducted at a temperature as low as about 100° C., about 110° C., about 120° C., about 130° C., about 140° C., about 150° C., about 160° C., or about 170° C., or at a temperature as high as about 180° C., about 190° C., about 200° C., about 210° C., about 220° C., about 230° C., about 240° C., or about 250° C., or within any range defined between any two of the foregoing values, such as about 100° C. to about 250° C., about 110° C. to about 240° C., about 120° C. to about 230° C., about 130° C. to about 220° C., about 140° C. to about 210° C., about 150° C. to about 200° C., about 160° C. to about 190° C., about 170° C. to about 180° C., about 120° C. to about 130° C., about 110° C. to about 180° C., or about 120° C. to about 250° C., for example. Preferably, the reactants are heated to a temperature from about 120° C. to about 200° C. More preferably, the reactants are heated to a temperature from about 150° C. to about 180° C.

Pressure is not critical. Convenient operating pressures may range from about 10 KPa to about 4,000 KPa, and preferably around ambient pressure, or about 100 KPa to about 250 KPa.

The reaction is carried out in a liquid phase reactor. The liquid phase reactor may be a semi-batch or continuously stirred tank reactor (CSTR). The reaction may be carried out as a batch process or as a continuous process.

The volatile products of the reaction, including the trifluoroiodomethane, may be condensed and collected, thus separating the trifluoroiodomethane from the non-volatile metal salt byproduct (MX, Eq. 1).

The composition of the volatile organic products of the reaction may be measured by gas chromatography (GC) and gas chromatography-mass spectroscopy (GC-MS) analyses. Graph areas provided by the GC analysis for each of the volatile organic compounds may be combined to provide a GC area percentage (GC area %) of the total volatile organic compounds for each of the volatile organic compounds as a measurement of the relative concentrations of the volatile organic compounds produced in the reaction.

While this invention has been described as relative to exemplary designs, the present invention may be further modified within the spirit and scope of this disclosure. Further, this application is intended to cover such departures from the present disclosure as come within known or customary practice in the art to which this invention pertains.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

EXAMPLES

Comparative Example 1

Decarboxylative Iodination of Trifluoroacetic Acid without a Metal Fluoride

In this Example, the manufacture of trifluoroiodomethane from trifluoroacetic acid ($CF_3COOH$) and iodine ($I_2$) without a metal fluoride is demonstrated for comparison purposes. Iodine in an amount of 46.7 g and 8.4 g of copper iodide catalyst were added to a 300-mL reactor from Parr Instrument Company, Moline, Ill. The reactor was equipped with a condenser. The reactor was pressure tested to 300 psig, and then evacuated. Sulfolane in an amount of 60 mL was added to the reactor, followed by 13.4 mL of trifluoroacetic acid to form a reactant mixture having a mole ratio of trifluoroacetic acid to iodine of about 0.95:1. The reactants, catalyst, and the solvent were obtained from Sigma-Aldrich Corp., St. Louis, Mo. and used without further purification.

The reactant mixture was heated to about 175° C. Volatile gaseous products and byproducts were produced as the reaction proceeded. The pressure in the reactor was monitored until there was no further increase in pressure, indicating that the reaction reached completion. The volatile gases exiting the condenser were collected in a product collection cylinder cooled in dry ice.

The composition of the organic compounds in the volatile gases collected in the product collection cylinder was measured by gas chromatography (GC). Graph areas provided by the GC analysis for each of the organic compounds were combined to provide a GC area percentage (GC area %) of the total organic compounds for each of the organic compounds as a measurement of the relative concentrations of the organic compounds. The GC analysis indicated no formation of trifluoroiodomethane.

Example 2

Decarboxylative Iodination of Trifluoroacetic Acid with a Metal Fluoride

In this Example, the manufacture of trifluoroiodomethane from trifluoroacetic acid ($CF_3COOH$) and iodine ($I_2$) in the presence of a metal fluoride is demonstrated. Iodine in an amount of 46.7 g, 11.2 g of potassium fluoride and 8.4 g of copper iodide catalyst were added to a 300-mL reactor from Parr Instrument Company, Moline, Ill. The reactor was equipped with a condenser. The reactor was pressure tested to 300 psig, and then evacuated. Sulfolane in an amount of 60 mL was added to the reactor, followed by 13.4 mL of trifluoroacetic acid to form a reactant mixture having a mole ratio of trifluoroacetic acid to iodine of about 0.95:1 and a mole ratio of trifluoroacetic acid to metal fluoride of about 0.91:1. The reactants, catalyst, and the solvent were obtained from Sigma-Aldrich Corp., St. Louis, Mo. and used without further purification. The potassium fluoride in spray-dried powder form was obtained from Honeywell Research Chemicals and was used without further purification.

The reactant mixture was heated to about 175° C. Volatile gaseous products and byproducts were produced as the reaction proceeded. The pressure in the reactor was monitored until there was no further increase in pressure, indicating that the reaction reached completion. The volatile gases exiting the condenser were collected in a product collection cylinder cooled in dry ice.

The composition of the organic compounds in the volatile gases collected in the product collection cylinder was measured by gas chromatography (GC). Graph areas provided by the GC analysis for each of the organic compounds were combined to provide a GC area percentage (GC area %) of the total organic compounds for each of the organic compounds as a measurement of the relative concentrations of the organic compounds. The GC analysis indicated that trifluoroiodomethane made up 47.21 GC area %, trifluoromethane made up 50.51 GC area %, with other organic compounds making up 2.28 GC area %. Thus, the presence of the metal fluoride enabled significant production of trifluoroiodomethane from trifluoroacetic acid in a single-step method. The significant formation of trifluoromethane can be attributed to the presence of the hydrogen atom on trifluoroacetic acid.

Aspects

Aspect 1 is a process for producing trifluoroiodomethane ($CF_3I$), the process comprising providing trifluoroacetic acid, an iodine source, a metal catalyst, a metal fluoride and a solvent; and reacting the trifluoroacetic acid, the iodine source, and the metal fluoride in the presence of the metal catalyst and the solvent to produce trifluoroiodomethane.

Aspect 2 is the process of Aspect 1, wherein the metal fluoride comprises at least one selected from the group of lithium fluoride, potassium fluoride, sodium fluoride, rubidium fluoride, calcium fluoride, and magnesium fluoride.

Aspect 3 is the process of Aspect 1, wherein the metal fluoride consists of at least one selected from the group of lithium fluoride, potassium fluoride, sodium fluoride, rubidium fluoride, calcium fluoride, and magnesium fluoride.

Aspect 4 is the process of Aspect 2, wherein the metal fluoride consists of lithium fluoride.

Aspect 5 is the process of Aspect 2, wherein the metal fluoride consists of potassium fluoride.

Aspect 6 is the process of Aspect 2, wherein the metal fluoride consists of sodium fluoride.

Aspect 7 is the process of Aspect 2, wherein the metal fluoride consists of rubidium fluoride.

Aspect 8 is the process of Aspect 2, wherein the metal fluoride consists of calcium fluoride.

Aspect 9 is the process of Aspect 2, wherein the metal fluoride consists of magnesium fluoride.

Aspect 10 is the process of any of Aspects 1-9, wherein in the providing step, the metal fluoride is in the form of a spray-dried powder.

Aspect 11 is the process of any of Aspects 1-10, wherein in the providing step, a mole ratio of trifluoroacetic acid to the metal fluoride is from about 0.1:1 to about 2.0:1.

Aspect 12 is the process of any of Aspects 1-10, wherein in the providing step, a mole ratio of trifluoroacetic acid to the metal fluoride is from about 0.8:1 to about 1.5:1.

Aspect 13 is the process of any of Aspects 1-10, wherein in the providing step, a mole ratio of trifluoroacetic acid to the metal fluoride is from about 1:1 to about 1.2:1.

Aspect 14 is the process of any of Aspects 1-13, wherein in the providing step, the iodine source comprises at least one selected from the group of iodine, iodine monochloride, iodine monofluoride, and iodine monobromide.

Aspect 15 is the process of any of Aspects 1-13, wherein in the providing step, the iodine source consists of at least one selected from the group of iodine, iodine monochloride, iodine monofluoride, and iodine monobromide.

Aspect 16 is the process of any of Aspects 1-13, wherein in the providing step, the iodine source consists of iodine.

Aspect 17 is the process of any of Aspects 1-13, wherein in the providing step, iodine source consists iodine monochloride.

Aspect 18 is the process of any of Aspects 1-13, wherein in the providing step, iodine source consists of iodine monofluoride.

Aspect 19 is the process of any of Aspects 1-13, wherein in the providing step, iodine source consists of iodine monobromide.

Aspect 20 is the process of any of Aspects 1-19, wherein in the providing step, a mole ratio of the trifluoroacetic acid to the iodine source is from about 0.1:1 to about 2.0:1.

Aspect 21 is the process of any of Aspects 1-19, wherein in the providing step, a mole ratio of the trifluoroacetic acid to the iodine source is from about 0.8:1 to about 1.5:1.

Aspect 22 is the process of any of Aspects 1-19, wherein in the providing step, a mole ratio of the trifluoroacetic acid to the iodine source is from about 1:1 to about 1.2:1.

Aspect 23 is the process of any of Aspects 1-22, wherein in the providing step, the metal catalyst comprises at least one selected from the group of copper (I) iodide, ferrous chloride, and zinc (II) iodide.

Aspect 24 is the process of any of Aspects 1-22, wherein in the providing step, the metal catalyst consists of at least one selected from the group of copper (I) iodide, ferrous chloride, and zinc (II) iodide.

Aspect 25 is the process of any of Aspects 1-22, wherein in the providing step, the metal catalyst consists of copper (I) iodide.

Aspect 26 is the process of any of Aspects 1-22, wherein in the providing step, the metal catalyst consists of ferrous chloride.

Aspect 27 is the process of any of Aspects 1-22, wherein in the providing step, the metal catalyst consists of zinc (II) iodide.

Aspect 28 is the process of any of Aspects 1-27, wherein in the providing step, the catalyst is provided for the reaction at a mole percent of the trifluoroacetic acid of from about 0.5% to about 50%.

Aspect 29 is the process of any of Aspects 1-27, wherein in the providing step, the catalyst is provided for the reaction at a mole percent of the trifluoroacetic acid of from about 0.5% to about 35%.

Aspect 30 is the process of any of Aspects 1-27, wherein in the providing step, the catalyst is provided for the reaction at a mole percent of the trifluoroacetic acid of from about 10% to about 30%.

Aspect 31 is the process of any of Aspects 1-27, wherein in the providing step, the catalyst is provided for the reaction at a mole percent of the trifluoroacetic acid of from about 20% to about 30%.

Aspect 32 is the process of any of Aspects 1-27, wherein in the providing step, the catalyst is provided for the reaction at a mole percent of the trifluoroacetic acid of about 25%.

Aspect 33 is the process of any of Aspects 1-32, wherein in the providing step, the solvent is at least one selected from the group of an ionic liquid and a polar aprotic solvent.

Aspect 34 is the process of any of Aspects 1-33, wherein in the providing step, the solvent is at least one selected from the group of imidazolium salts, caprolactamium hydrogen sulfate, sulfolane, N,N-dimethylacetamide, N-methyl-2-pyrrolidone (NMP), and dimethyl sulfone.

Aspect 35 is the process of Aspect 34, wherein in the providing step, the solvent consists of sulfolane.

Aspect 36 is the process of any of Aspects 1-35, wherein in the reacting step, the trifluoroacetic acid, the iodine source, the metal fluoride and the solvent are at a temperature from 100° C. to 250° C.

Aspect 37 is the process of any of Aspects 1-35, wherein in the reacting step, the trifluoroacetic acid, the iodine source, the metal fluoride and the solvent are at a temperature from 120° C. to 200° C.

Aspect 38 is the process of any of Aspects 1-35, wherein in the reacting step, the trifluoroacetic acid, the iodine source, the metal fluoride and the solvent are at a temperature from 150° C. to 180° C.

Aspect 39 is a process for producing trifluoroiodomethane ($CF_3I$), the process comprising mixing trifluoroacetic acid, an iodine source, a metal catalyst, a metal fluoride, and a solvent; and heating the trifluoroacetic acid, the iodine source, the metal catalyst the metal fluoride, and the solvent to react the trifluoroacetic acid, the iodine source, and the metal fluoride to produce trifluoroiodomethane and a metal salt.

Aspect 40 is the process of Aspect 39, further including separating the trifluoroiodomethane from the metal salt.

Aspect 41 is the process of either of Aspects 39 or 40, wherein the process is a continuous process.

Aspect 42 is the process of either of Aspects 39 or 40, wherein the process is a batch process.

Aspect 43 is the process of any of Aspects 39-42, wherein the metal fluoride comprises at least one selected from the group of lithium fluoride, potassium fluoride, sodium fluoride, rubidium fluoride, calcium fluoride, and magnesium fluoride.

Aspect 44 is the process of any of Aspects 39-42, wherein the metal fluoride consists of at least one selected from the group of lithium fluoride, potassium fluoride, sodium fluoride, rubidium fluoride, calcium fluoride, and magnesium fluoride.

Aspect 45 is the process of any of Aspects 39-42, wherein the metal fluoride consists of lithium fluoride.

Aspect 46 is the process of any of Aspects 39-42, wherein the metal fluoride consists of potassium fluoride.

Aspect 47 is the process of any of Aspects 39-42, wherein the metal fluoride consists of sodium fluoride.

Aspect 48 is the process of any of Aspects 39-42, wherein the metal fluoride consists of rubidium fluoride.

Aspect 49 is the process of any of Aspects 39-42, wherein the metal fluoride consists of calcium fluoride.

Aspect 50 is the process of any of Aspects 39-42, wherein the metal fluoride consists of magnesium fluoride.

Aspect 51 is the process of any of Aspects 39-50, wherein the metal fluoride is in the form of a spray-dried powder.

Aspect 52 is the process of any of Aspects 39-51, wherein a mole ratio of trifluoroacetic acid to the metal fluoride is from about 0.1:1 to about 2.0:1.

Aspect 53 is the process of any of Aspects 39-51, wherein a mole ratio of trifluoroacetic acid to the metal fluoride is from about 0.8:1 to about 1.5:1.

Aspect 54 is the process of any of Aspects 39-51, wherein a mole ratio of trifluoroacetic acid to the metal fluoride is from about 1:1 to about 1.2:1.

Aspect 55 is the process of any of Aspects 39-54, wherein the iodine source comprises at least one selected from the group of iodine, iodine monochloride, iodine monofluoride, and iodine monobromide.

Aspect 56 is the process of any of Aspects 39-54, wherein the iodine source consists of at least one selected from the group of iodine, iodine monochloride, iodine monofluoride, and iodine monobromide.

Aspect 57 is the process of any of Aspects 39-54, wherein the iodine source consists of iodine.

Aspect 58 is the process of any of Aspects 39-54, wherein the iodine source consists iodine monochloride.

Aspect 59 is the process of any of Aspects 39-54, wherein the iodine source consists of iodine monofluoride.

Aspect 60 is the process of any of Aspects 39-54, wherein the iodine source consists of iodine monobromide.

Aspect 61 is the process of any of Aspects 39-60, wherein a mole ratio of the trifluoroacetic acid to the iodine source is from about 0.1:1 to about 2.0:1.

Aspect 62 is the process of any of Aspects 39-60, wherein a mole ratio of the trifluoroacetic acid to the iodine source is from about 0.8:1 to about 1.5:1.

Aspect 63 is the process of any of Aspects 39-60, wherein a mole ratio of the trifluoroacetic acid to the iodine source is from about 1:1 to about 1.2:1.

Aspect 64 is the process of any of Aspects 39-63, wherein the metal catalyst comprises at least one selected from the group of copper (I) iodide, ferrous chloride, and zinc (II) iodide.

Aspect 65 is the process of any of Aspects 39-63, wherein the metal catalyst consists of at least one selected from the group of copper (I) iodide, ferrous chloride, and zinc (II) iodide.

Aspect 66 is the process of any of Aspects 39-63, wherein the metal catalyst consists of copper (I) iodide.

Aspect 67 is the process of any of Aspects 39-63, wherein the metal catalyst consists of ferrous chloride.

Aspect 68 is the process of any of Aspects 39-63, wherein the metal catalyst consists of zinc (II) iodide.

Aspect 69 is the process of any of Aspects 39-68, wherein the catalyst is provided for the reaction at a mole percent of the trifluoroacetic acid of from about 0.5% to about 50%.

Aspect 70 is the process of any of Aspects 39-68, wherein the catalyst is provided for the reaction at a mole percent of the trifluoroacetic acid of from about 0.5% to about 35%.

Aspect 71 is the process of any of Aspects 39-68, wherein the catalyst is provided for the reaction at a mole percent of the trifluoroacetic acid of from about 10% to about 30%.

Aspect 72 is the process of any of Aspects 39-68, wherein the catalyst is provided for the reaction at a mole percent of the trifluoroacetic acid of from about 20% to about 30%.

Aspect 73 is the process of any of Aspects 39-68, wherein the catalyst is provided for the reaction at a mole percent of the trifluoroacetic acid of about 25%.

Aspect 74 is the process of any of Aspects 39-73, wherein the solvent is at least one selected from the group of an ionic liquid and a polar aprotic solvent.

Aspect 75 is the process of any of Aspects 39-73, wherein the solvent is at least one selected from the group of imidazolium salts, caprolactamium hydrogen sulfate, sulfolane, N,N-dimethylacetamide, N-methyl-2-pyrrolidone (NMP), and dimethyl sulfone.

Aspect 76 is the process of Aspect 75, wherein the solvent consists of sulfolane.

Aspect 77 is the process of any of Aspects 39-76, wherein the trifluoroacetic acid, the iodine source, the metal fluoride and the solvent are heated to a temperature from 100° C. to 250° C.

Aspect 78 is the process of any of Aspects 39-76, wherein the trifluoroacetic acid, the iodine source, the metal fluoride and the solvent are heated to a temperature from 120° C. to 200° C.

Aspect 79 is the process of any of Aspects 39-76, wherein the trifluoroacetic acid, the iodine source, the metal fluoride and the solvent are heated to a temperature from 150° C. to 180° C.

What is claimed is:

1. A process for producing trifluoroiodomethane ($CF_3I$), the process comprising:
   providing trifluoroacetic acid, an iodine source, a metal catalyst, a metal fluoride and a solvent; and
   reacting the trifluoroacetic acid, the iodine source, and the metal fluoride in the presence of the metal catalyst and the solvent to produce trifluoroiodomethane, wherein in the providing step, the metal fluoride is in the form of a spray-dried powder.

2. The process of claim 1, wherein the metal fluoride comprises at least one selected from the group of lithium fluoride, potassium fluoride, sodium fluoride, rubidium fluoride, calcium fluoride, and magnesium fluoride.

3. The process of claim 1, wherein in the providing step, a mole ratio of the trifluoroacetic acid to the metal fluoride is from about 0.1:1 to about 2.0:1.

4. The process of claim 1, wherein the iodine source comprises at least one selected from the group of iodine, iodine monochloride, iodine monofluoride, and iodine monobromide.

5. The process of claim 1, wherein in the providing step, a mole ratio of the trifluoroacetic acid to the iodine source is from about 0.1:1 to about 2:1.

6. The process of claim 1, wherein the metal catalyst comprises at least one selected from the group of copper (I) iodide, ferrous chloride, and zinc (II) iodide.

7. The process of claim 1, wherein in the providing step, the catalyst is provided for the reaction at a mole percent of the trifluoroacetic acid of from about 0.5% to about 50%.

8. The process of claim 1, wherein the solvent is at least one selected from the group of an ionic liquid and a polar aprotic solvent.

9. The process of claim 8, wherein the solvent is at least one selected from the group of imidazolium salts, caprolactamium hydrogen sulfate, sulfolane, N,N-dimethylacetamide, N-methyl-2-pyrrolidone (NMP), and dimethyl sulfone.

10. The process of claim 1, wherein in the reacting step, the trifluoroacetic acid, the iodine source, the metal fluoride and the solvent are at a temperature from 100° C. to 250° C.

11. A process for producing trifluoroiodomethane ($CF_3I$), the process comprising:

mixing trifluoroacetic acid, an iodine source, a metal catalyst, a metal fluoride, and a solvent, wherein the metal fluoride is in the form of a spray-dried powder; and heating the trifluoroacetic acid, the iodine source, the metal catalyst, the metal fluoride, and the solvent to react the trifluoroacetic acid, the iodine source, and the metal fluoride to produce trifluoroiodomethane and a metal salt.

12. The process of claim 11, further including separating the trifluoroiodomethane from the metal salt.

13. The process of claim 11, wherein the process is a continuous process.

14. The process of claim 11, wherein the process is a batch process.

15. The process of claim 11, wherein the metal fluoride comprises at least one selected from the group of lithium fluoride, potassium fluoride, sodium fluoride, rubidium fluoride, calcium fluoride, and magnesium fluoride.

16. The process of claim 11, wherein the iodine source comprises at least one selected from the group of iodine, iodine monochloride, iodine monofluoride, and iodine monobromide.

17. The process of claim 11, wherein the metal catalyst comprises at least one selected from the group of copper (I) iodide, ferrous chloride, and zinc (II) iodide.

18. The process of claim 11, wherein the trifluoroacetic acid, the iodine source, the metal fluoride and the solvent are heated to a temperature from 100° C. to 250° C.

* * * * *